United States Patent
Herold et al.

(10) Patent No.: US 9,532,727 B2
(45) Date of Patent: Jan. 3, 2017

(54) METHOD AND APPARATUS FOR ILLUMINATING THE INTERIOR OF A MEDICAL IMAGING DEVICE

(75) Inventors: Mark Douglas Herold, Stow, OH (US); Daniel David Judkins, Richmond Heights, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1351 days.

(21) Appl. No.: 12/994,014

(22) PCT Filed: May 29, 2009

(86) PCT No.: PCT/IB2009/052285
§ 371 (c)(1),
(2), (4) Date: Nov. 22, 2010

(87) PCT Pub. No.: WO2009/147608
PCT Pub. Date: Dec. 10, 2009

(65) Prior Publication Data
US 2011/0082348 A1    Apr. 7, 2011

Related U.S. Application Data

(60) Provisional application No. 61/059,372, filed on Jun. 6, 2008.

(51) Int. Cl.
*A61B 1/06* (2006.01)
*A61B 5/055* (2006.01)
*A61B 6/03* (2006.01)
*G01R 33/28* (2006.01)
*A61B 5/00* (2006.01)

(52) U.S. Cl.
CPC .............. *A61B 5/055* (2013.01); *A61B 6/032* (2013.01); *A61B 6/037* (2013.01); *G01R 33/28* (2013.01); *A61B 5/0033* (2013.01); *A61B 5/742* (2013.01); *G01R 33/288* (2013.01)

(58) Field of Classification Search
USPC .......................... 600/249, 407, 410, 418, 425
See application file for complete search history.

(56) References Cited

U.S. PATENT DOCUMENTS

| | | | |
|---|---|---|---|
| 4,070,568 A * | 1/1978 | Gala | 362/311.09 |
| 4,613,926 A | 9/1986 | Heitman et al. | |
| 4,901,141 A * | 2/1990 | Costello | 348/77 |
| 5,336,897 A * | 8/1994 | Watanabe et al. | 250/551 |
| 5,339,813 A | 8/1994 | DeYoe et al. | |
| 5,355,885 A * | 10/1994 | Tsuda et al. | 600/418 |
| 5,469,488 A * | 11/1995 | Ono | 378/15 |
| 5,877,732 A | 3/1999 | Ziarati | |
| 6,175,354 B1 * | 1/2001 | Blissett et al. | 345/110 |
| 6,290,357 B1 * | 9/2001 | Massengill et al. | 351/209 |

(Continued)

FOREIGN PATENT DOCUMENTS

| | | |
|---|---|---|
| CN | 1550207 A | 1/2004 |
| DE | 4225433 A1 | 2/1994 |

(Continued)

*Primary Examiner* — Zade Coley (57) ABSTRACT

A method and apparatus for illuminating the interior of a medical imaging device is provided. The method and apparatus may convey information to the patient within the scanning tube via the use of different colors or brightness of illuminating light and images and/or text may be provided.

19 Claims, 5 Drawing Sheets

(56) References Cited

U.S. PATENT DOCUMENTS

| | | | |
|---|---|---|---|
| 6,294,915 B1 | 9/2001 | Murphy et al. | |
| 6,426,991 B1* | 7/2002 | Mattson et al. | 378/19 |
| 7,331,698 B2* | 2/2008 | Gosswein et al. | 362/572 |
| 7,702,375 B2* | 4/2010 | Boninger et al. | 600/407 |
| 7,823,306 B1* | 11/2010 | Kersten et al. | 40/436 |
| 2003/0128034 A1* | 7/2003 | Haumann | 324/318 |
| 2005/0004444 A1 | 1/2005 | Boninger et al. | |
| 2005/0119559 A1* | 6/2005 | Van Vaals et al. | 600/425 |
| 2008/0009696 A1 | 1/2008 | Hempel | |
| 2009/0093705 A1* | 4/2009 | Vangdal | 600/410 |
| 2009/0262551 A1* | 10/2009 | Trowell et al. | 362/551 |

FOREIGN PATENT DOCUMENTS

| | | | |
|---|---|---|---|
| DE | 19639923 A1 | 7/1997 | |
| DE | 10008808 A1 | 6/2001 | |
| DE | 10122826 A1 | 6/2002 | |
| DE | 10334326 A1 | 2/2005 | |
| JP | 2098003 A2 | 4/1990 | |
| JP | 3146029 A | 6/1991 | |
| JP | 5146423 A | 6/1993 | |
| JP | 08131420 A | 5/1996 | |
| WO | 0122108 A1 | 3/2001 | |
| WO | 2008017879 A2 | 2/2008 | |
| WO | WO 2008017879 A2 * | 2/2008 | G01R 33/28 |

\* cited by examiner

METHOD AND APPARATUS FOR ILLUMINATING THE INTERIOR OF A MEDICAL IMAGING DEVICE

CROSS REFERENCE TO RELATED APPLICATIONS

This application claims the benefit of U.S. provisional application Ser. No. 61/059,372 filed Jun. 6, 2008, which is incorporated herein by reference.

The present application relates generally to the imaging arts and more particularly to an apparatus for illuminating the interior of a medical imaging device. The application subject matter finds particular use with computed tomography (CT) imaging devices and will be described with particular reference thereto, but could also be used with other medical imaging devices, such as single-photon emission computed tomography (SPECT), magnetic resonance (MR), or positron emission tomography (PET) imaging devices.

During many such medical imaging procedures, a patient is often placed either partially or fully within an examination region of the imaging device. The examination region often takes the form of a cylindrical or toroidal scanning tube. Being within the scanning tube can cause a patient to feel claustrophobic or otherwise stressed. In addition, once a patient is placed within the scanning tube, it can be difficult for medical personnel to convey information to the patient. For example, it can be difficult to instruct the patient to hold his or her breath, or convey information regarding the status of the imaging procedure.

According to one aspect of the present invention, an apparatus is provided for illuminating the interior of a medical imaging device. According to another aspect of the present invention, an apparatus is provided for conveying information to the patient within the scanning tube via the use of different colors of illuminating light, images and/or text.

Illuminating the scanning tube and/or projecting images onto the scanning tube reduces the patient's stress and feelings of claustrophobia. Another advantage resides in that the illumination of the interior of the scanning tube allows the technologist to observe the patient within the scanning tube during the scanning procedure. Yet another advantage resides in the ability to convey information to the patient within the scanning tube. Numerous additional advantages and benefits will become apparent to those of ordinary skill in the art upon reading the following detailed description of the preferred embodiments.

The invention may take form in various components and arrangements of components, and in various process operations and arrangements of process operations.

The drawings are only for the purpose of illustrating preferred embodiments and are not to be construed as limiting the invention.

Figure 1:
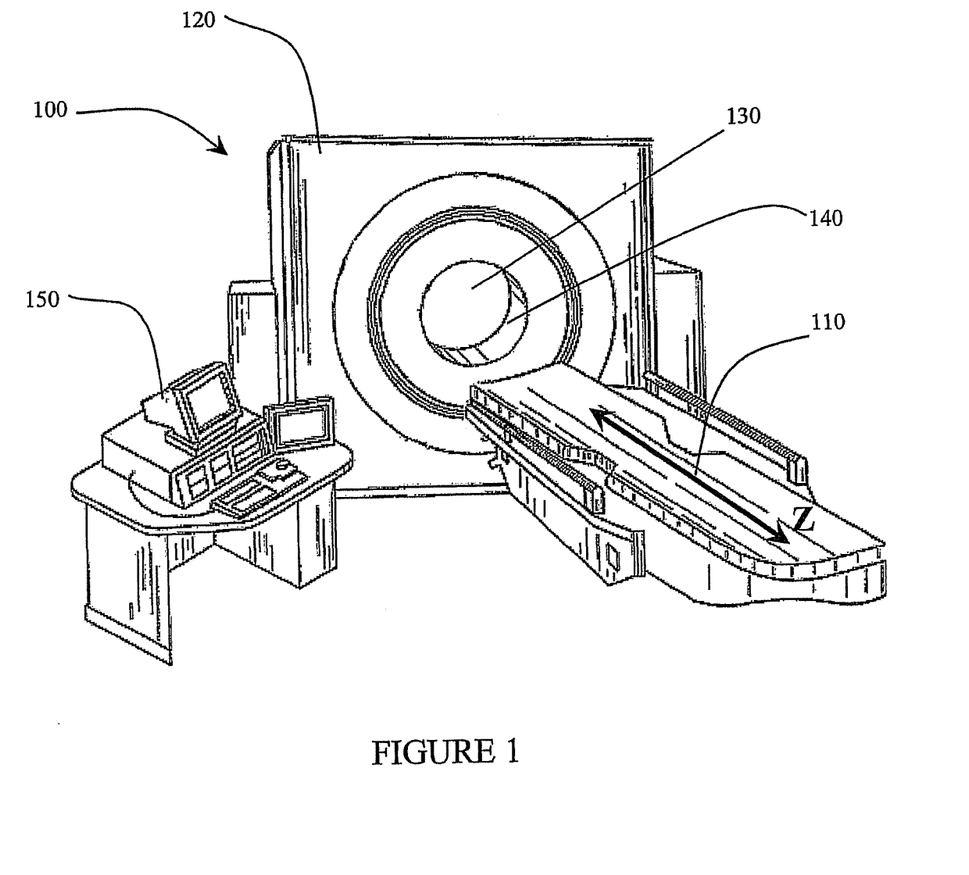
FIG. 1 is an exemplary CT imaging system.

The medical imaging system and apparatus of the present application is generally any medical imaging system, for example, a CT, SPECT, MR or PET imaging system. More specifically, with reference to FIG. 1, in an exemplary embodiment, the medical imaging system 100 is a CT imaging system. The CT imaging system 100 includes a subject support 110, such as a table or couch, which supports and positions a subject being examined and/or imaged, such as a patient. The CT imaging system 100 includes a stationary gantry 120 with a rotating gantry (not shown) mounted inside. The stationary gantry 120 defines a subject-receiving aperture 130. A scanning tube 140 extends through the stationary gantry 120 and partially defines the subject-receiving aperture 130. The scanning tube 140 defines an examination region. The scanning tube 140 may be an integral part of the stationary gantry 120 or it may be a separate component from the stationary gantry 120. The subject support 110 is linearly movable along a Z-axis relative to the scanning tube 140, thus allowing the subject support 110 and the patient when placed thereon to be moved within and removed from the scanning tube 140.

The rotating gantry is adapted to rotate around the scanning tube 140 and the patient when located therein. The rotating gantry may rotate at the same time as the subject support 110 moves linearly, or the rotating gantry may rotate as the subject support 110 remains stationary, depending upon the medical imaging procedure being conducted. One or more x-ray sources 410 (as shown for example in FIG. 4) are mounted on the rotating gantry to produce an x-ray beam directed through the scanning tube 140 and the patient when located therein. The x-ray beam is then detected by one or more x-ray detector units 420 (as shown for example in FIG. 4) which are also mounted on the rotating gantry. A computer 150 controls the operation of the CT imaging system, including the operation of the subject support 110 and rotating gantry. The data acquired by the one or more detector units is reconstructed to form an image that can optionally be displayed on the computer 150.

Figure 2:
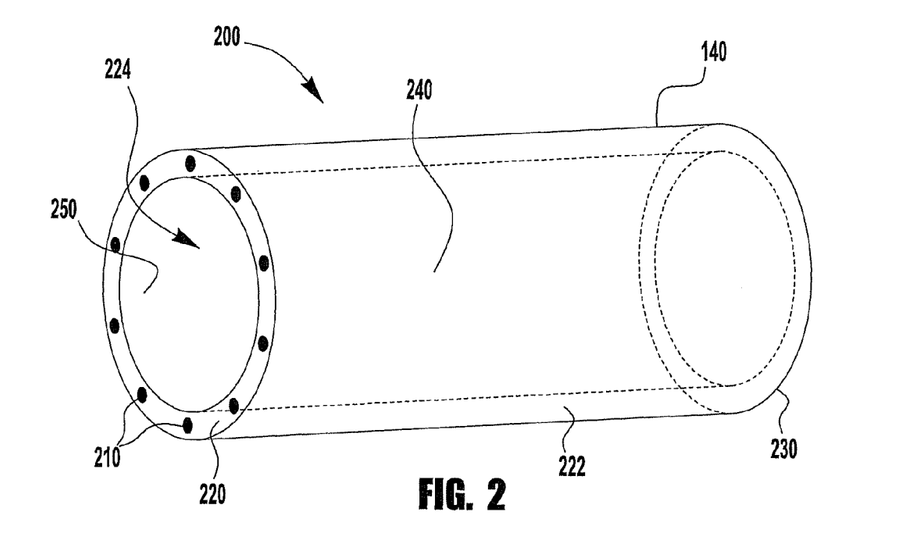
FIG. 2 is a perspective view of a first embodiment of a scanning tube illumination apparatus with the stationary gantry removed for illustrative purposes.

Referring to FIG. 2, a first embodiment of a scanning tube illumination apparatus 200 is shown. The illumination apparatus 200 generally includes one or more light sources 210 located adjacent to or in proximity of the end surface 220 of the scanning tube 140. The scanning tube 140 of the illumination apparatus 200 is a cylindrical tube with a side wall 222 defining a cylindrically shaped interior 224 for receipt of a patient. When illuminated, the light source(s) 210 emit light into the end surface 220 of the scanning tube 140. The light from the light sources 210 travels along the length of the side wall 222 of the scanning tube 140, thereby illuminating the side wall 222 and the interior 224 of the scanning tube 140 as viewed by a patient within the scanning tube 140. It should be understood that the scanning tube 140 of additional embodiments may have a variety of cross sectional shapes, such as rectangular, square, oval, as well as different sizes and configurations.

In various embodiments, the light sources 210 could be mounted directly to the end surface 220 via an adhesive, velcro, or some other mounting method. In additional embodiments, the light sources 210 could be embedded into the end surface 220 or other portion of the scanning tube

140. In yet additional embodiments, the light sources 210 could be located in proximity of the end surface 220, but not be mounted directly to or embedded into the end surface 220, such as for example via a frame or other support structure. Preferably, the light sources are selected and adapted so that the x-ray scatter related to the light sources does not adversely effect the imaging quality of the medical imaging system 100. While the illustrated embodiment of the illumination apparatus 200 includes ten light sources 210, any number of light sources could be used in additional embodiments. In additional embodiments, a suitable light source could take the form of one unitary complete shape, such as a circular or oval-shaped ring, which corresponds to the cross-sectional shape of the scanning tube 140. In further additional embodiments, the light source could be a plurality of segments, such as arcuate portions, located adjacent to or in proximity of the end surface 220 of the scanning tube 140 at spaced apart intervals. While the light sources 210 of the illustrated embodiment of illumination apparatus 200 are located adjacent to or in proximity of the end surface 220 of the scanning tube 140, light sources 210 could be located adjacent to or in proximity of side wall 222 and/or end surface 230 in additional embodiments.

The light sources 210 of the illustrated embodiment are light emitting diodes (LED). It should be understood, however, that additional light source types may be utilized in additional embodiments, such as gas discharge, including fluorescent or neon, electroluminescent, incandescent, including halogen, or other suitable light source types. The illuminating light provided by the light sources 210 may be continuous or non-continuous. The light sources 210 may emit a single color of light, such as white, or a variety of different colors of light, such as red, green, blue or any other color. Various embodiments of the illuminating apparatus 200 may include a plurality of light sources 210 emitting light of the same color, while additional embodiments may include a plurality of light sources each emitting light of a different color or selected from a group of colors. In certain embodiments, filters (not shown) may be employed to alter the color, brightness or other characteristic of the light emitted from the light sources 210. In yet additional embodiments of the lighting apparatus 200, the light sources 210 may be adapted to pulsate, cycle through various phases of different brightness or different colors, be coordinated with background sound or music, or have some other lighting effect to sooth or comfort the patient and help to alleviate or reduce their stress. Furthermore, in additional embodiments, light sources of various colors, such as red, green or blue, could be time modulated at a high frequency (e.g., 120 Hz or greater) to produce light of any color of the viewable spectrum.

Altering the brightness, color, or other characteristic of the light emitted from the light sources 210 may be employed to convey information to a patient within the scanning tube 140. For example, a certain color or brightness level of light could be used as an indicator to instruct the patient to hold his or her breath or perform some other action when the scanning tube 140 is illuminated with that pre-selected color or brightness level. Also, the light emitted from the light sources 210 could change in brightness or color to indicate different stages of the imaging procedure. For example, illuminating of the scanning tube 140 with red colored light could indicate to a patient that the medical imaging system 100 is scanning and illuminating of the scanning tube 140 with green colored light could indicate to the patient that the medical imaging system 100 is not scanning. Similarly, such message may be conveyed by sequencing light pulses in number and/or in length of the pulses.

The scanning tube 140 of the illustrated embodiment of the CT imaging system 100 is made of a thermoplastic, such as LEXAN. However, other materials may be used such as glass, other types of plastic, or other suitable materials.

The scanning tube 140 of the illustrated embodiment of the illumination apparatus 200 is transparent or nearly transparent allowing light to pass through it freely. In additional embodiments of the illumination apparatus 200, however, the outer surface 240 of the scanning tube 140 may be etched or frosted so as to render the scanning tube translucent (i.e., allowing light to pass through diffusely). The etched outer surface 240 of the scanning tube 140 serves to scatter the light emitted from the light sources 210 thereby evenly illuminating the scanning tube 140 as viewed by a patient inside the scanning tube 140. In additional embodiments, the inner surface 250 or both the inner surface 250 and outer surface 240 of the scanning tube 140 could be etched. The etching of the scanning tube can be accomplished through a variety of different methods, such as chemical etching or sand blasting. In additional embodiments, the scanning tube 140 may be coated with a paint or other substance that simulates the translucent qualities of etching. In yet additional embodiments, the scanning tube 140 may be clad or surrounded with a translucent material. Preferably but not necessarily, the structure chosen to make the scanning tube translucent is configured to minimize absorption of x-ray radiation by the structure, avoiding the need for more powerful x-ray sources 410.

Figure 3:
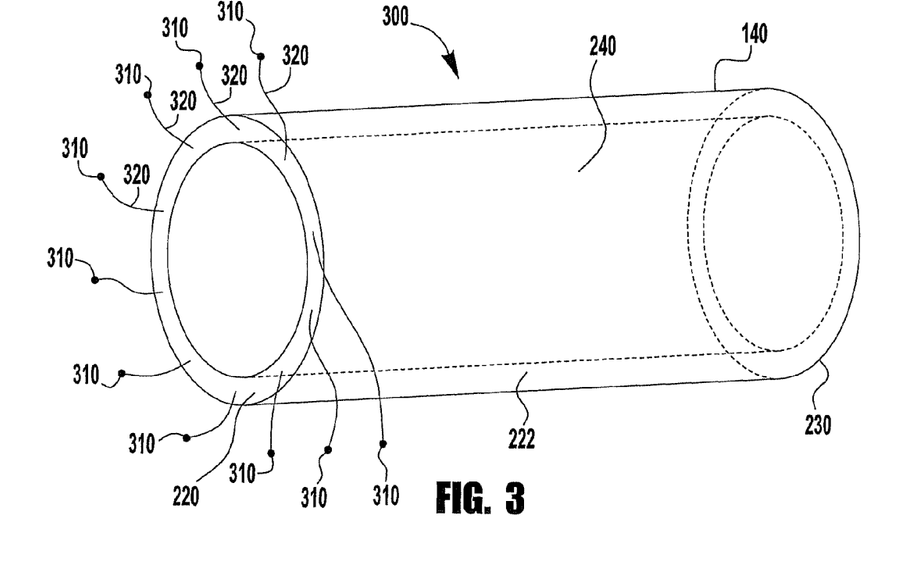
FIG. 3 is a perspective view of a second embodiment of the scanning tube illumination apparatus.

Referring now to FIG. 3, a second embodiment of a scanning tube illumination apparatus 300 is shown. The illumination apparatus 300 generally includes one or more light sources 310 located remotely from the end surface 220 of the scanning tube 140. Light emitted from the light sources 310 is transmitted to the end surface 220 of the scanning tube 140 by optical fibers 320. The light then travels along the length of the side wall 222 of the scanning tube 140, thereby illuminating the side wall 222 and the interior 224 of the scanning tube 140 as viewed by a patient within the scanning tube 140 similarly to the first embodiment of the illumination apparatus 200.

The optical fibers 320 can be made of glass, plastic or any other suitable material that allows the fiber to carry light along its length. The optical fibers 320 can be flexible, semi-rigid or rigid. The light sources 310 may be located within any portion of the CT imaging system 100 or may be located externally of the CT imaging system 100. The disclosure regarding the light sources 210 and scanning tube 140 of the illuminating apparatus 200 illustrated in FIG. 2 similarly applies to the light sources 310 and scanning tube 140 of the illuminating apparatus 300.

Figure 4:
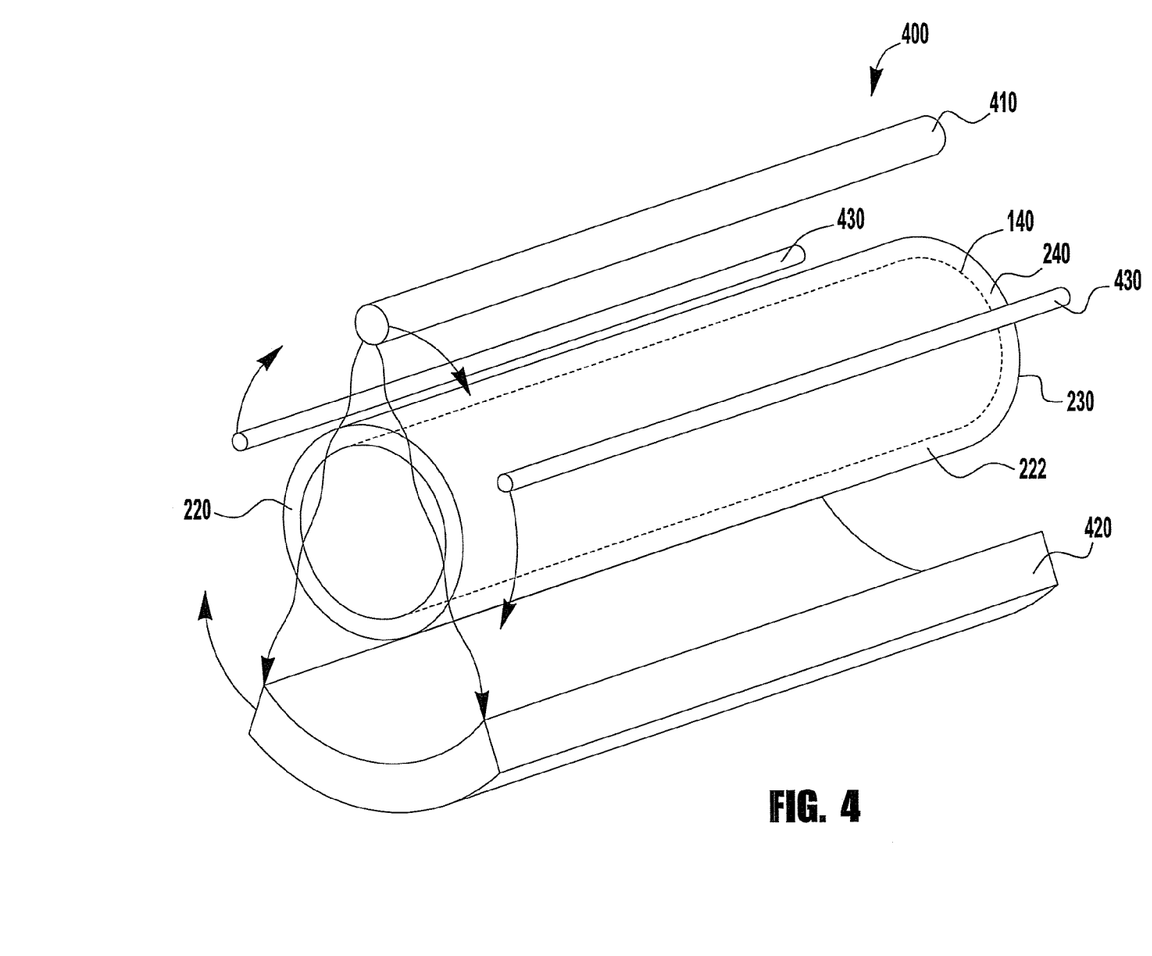
FIG. 4 is a perspective view of a third embodiment of the scanning tube illumination apparatus.

Referring now to FIG. 4, a third embodiment of a scanning tube illumination apparatus 400 is shown. The illumination apparatus 400 generally includes one or more light sources 430. When illuminated, the one or more light sources 430 shine light upon the outer surface 240 of the scanning tube 140. The illustrated embodiment of the lighting apparatus 400 includes a pair of light sources 430, but a single light source or any number of light sources could be used in additional embodiments. The light sources 430 of the illustrated embodiment are gas discharge light sources, such as fluorescent or neon light sources. It should be understood, however, that additional light source types may also be utilized, such as light-emitting diodes, electroluminescent light sources, incandescent light sources, including halogen, or other suitable light sources. While the light sources 430 of illumination apparatus 400 span the entire length of the scanning tube 140, it should be understood that the light sources 430 of additional embodiments may span only a portion of the scanning tube 140.

As discussed earlier, the CT imaging system 100 includes one or more x-ray sources 410 and one or more x-ray detector units 420. The x-ray source(s) 410 and x-ray detector unit(s) 420 are mounted to the rotating gantry (not shown). The x-ray source(s) 410 and x-ray detector unit(s) 420 are adapted to rotate around the scanning tube 140 on the rotating gantry. The light sources 430 of the illustrated embodiment are similarly mounted to the rotating gantry and are adapted to rotate in concert with the x-ray source(s) 410 and x-ray detector unit(s) 420 around the scanning tube 140. In various embodiments, the light sources 430 could be mounted to a different frame than the rotating gantry on which the x-ray source(s) 410 and x-ray detector unit(s) 420 are mounted. The x-ray source(s) 410 and x-ray detector unit(s) 420 in most conventional CT imaging systems rotate at rates of approximately one revolution per 0.5 seconds or faster. At such speeds, the illumination of the scanning tube 140 by the light sources 430 would have an even consistency as viewed by a patient within the scanning tube 140. However, it should be understood that the illumination apparatus 400 is not limited to any particular rotational speed as a variety of rotational speeds may be employed in various embodiments. In additional embodiments, the light sources 430 may rotate at a different speed than the x-ray source(s) 410 and x-ray detector unit(s) 420. In yet additional embodiments, the light sources 430 may be stationary and not rotate with respect to the scanning tube 140 at all.

The scanning tube 140 of the illumination apparatus 400 may be etched so as to render it translucent as already described in connection with other embodiments. In the lighting apparatus 400, due to the translucence of the scanning tube 140, a patient located within the scanning tube 140 can not clearly see the x-ray source(s) 410, x-ray detector unit(s) 420, light sources 430 or any other contents of the rotating gantry through the scanning tube 140.

Figure 5A:
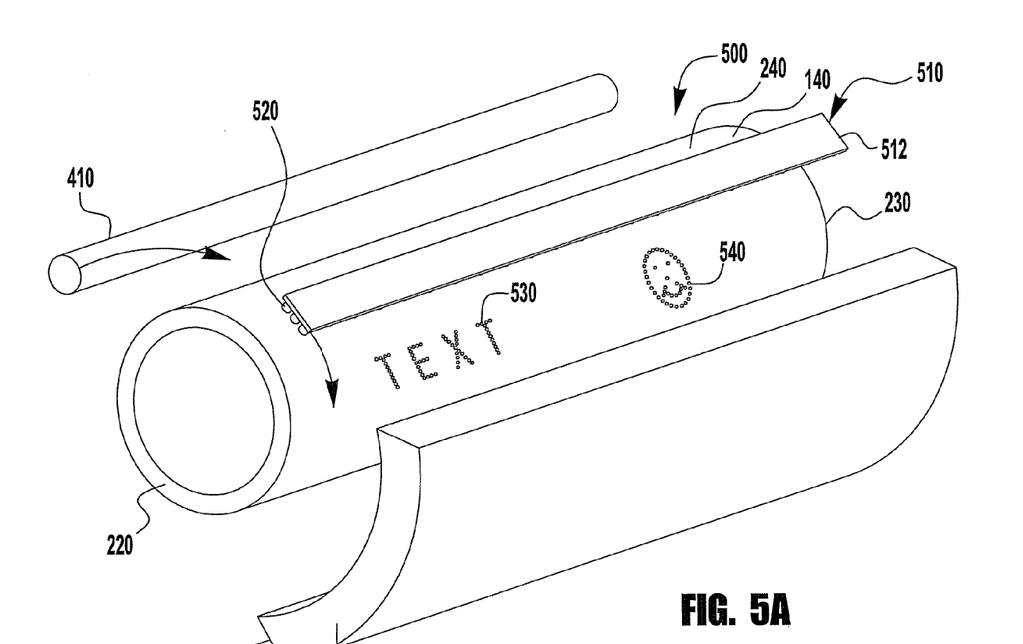
FIG. 5A is a perspective view of a fourth embodiment of the scanning tube illumination apparatus and including a light source array.

Referring now to FIG. 5A, a fourth embodiment of a scanning tube illumination apparatus 500 is shown. The illumination apparatus 500 generally includes a light source array 510. When illuminated, the light source array 510 shines light upon the outer surface 240 of the scanning tube 140. The illustrated embodiment of the lighting apparatus 400 includes a single light source array 510, but a pair of light source arrays or any number of light source arrays could be used in additional embodiments. The light source array 510 of the illustrated embodiment of lighting apparatus 500 includes a frame 512 or similar support that supports a plurality of light emitting diodes (LEDs) 520. It should be understood, however, that additional light source types may be utilized in additional embodiments, such as gas discharge, including fluorescent or neon, electroluminescent, incandescent, including halogen, or other suitable light source types. As illustrated, the exemplary light source array 510 of the illumination apparatus 500 spans the entire length of the scanning tube 140. However, it should be understood that the light source array(s) in additional embodiments may span only a portion of the scanning tube 140.

Figure 5B:
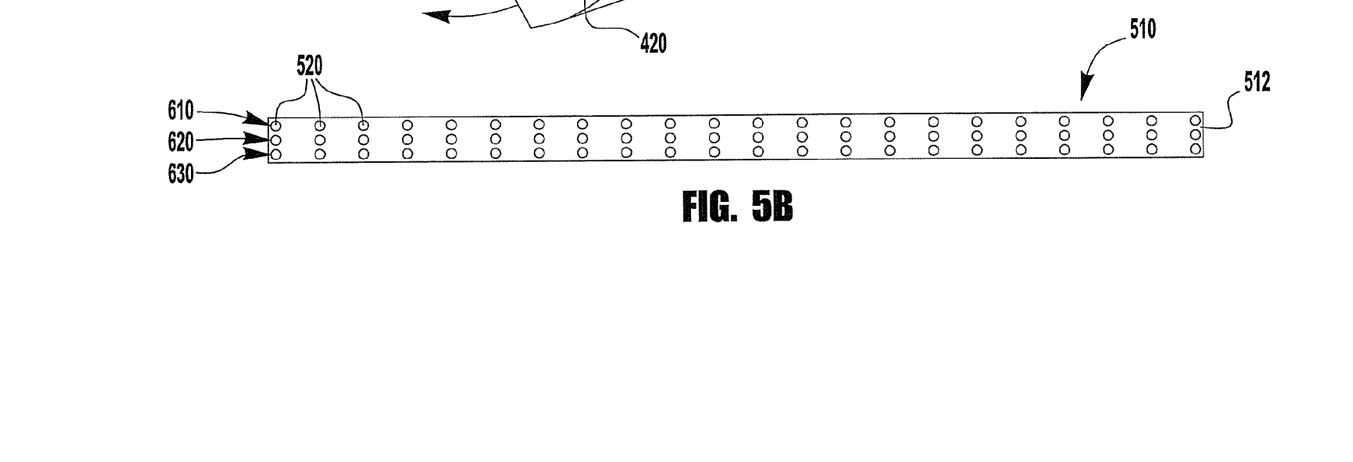
FIG. 5B is a perspective view of the light source array of FIG. 5A.

Referring now to FIG. 5B, the light source array 510 of the scanning tube illumination apparatus 500 is shown. The light source array of the illustrated embodiment includes three rows 610, 620, 630 of light emitting diodes 520. However, it should be understood that additional embodiments of the light source arrays may include one row or any number of rows of light emitting diodes 520. Row 610 of the illustrated embodiment of the light source array 510 includes red light emitting diodes 520, row 620 includes green light emitting diodes 520, and row 630 includes blue light emitting diodes 520. However, additional embodiments of the light source array 510 may include only one color of light emitting diodes 520 or may include light emitting diodes that emit a color of light other than red, green, or blue. In further additional embodiments, the light source array 510 may include light emitting diodes 520 that can each emit various colors of light. Each row 610, 620, 630 of the illustrated embodiment of the light source array 510 includes a total of twenty two light emitting diodes 520, however, the light source array 510 of additional embodiments may have any number of light emitting diodes 520.

The scanning tube 140 of the illumination apparatus 500 may be etched so as to render it translucent, as already described in connection with other embodiments. As discussed with the lighting apparatus 400 illustrated in FIG. 4, the light source array 510 of the illustrated embodiment is mounted to the rotating gantry and is adapted to rotate in concert with the x-ray source(s) 410 and x-ray detector unit(s) 420 around the scanning tube 140. In other embodiments, the light source array 510 could be mounted to a different frame than the rotating gantry on which the x-ray source(s) 410 and x-ray detector unit(s) 420 are mounted. The light source array 510 may rotate at a different speed than the x-ray source(s) 410 and x-ray detector unit(s) 420 or the light source array 510 may rotate while the x-ray source(s) 410 and x-ray detector unit(s) 420 remain stationary. Preferably, in such embodiments, the light source array 510, x-ray source(s) 410 and x-ray detector unit(s) 420 are controlled in such a manner that the light source array 150 is not in between the x-ray source(s) 410 and x-ray detector unit(s) 420 while the x-ray source(s) 410 are activated. In yet additional embodiments, the light source array 510 may be stationary and not rotate with respect to the scanning tube 140 at all.

As the light source array 510 rotates around the scanning tube 140, the light emitted from the light source array 510 illuminates the etched outer surface 240 of the scanning tube 140. Each of the light emitting diodes 520 of light source array 510 can be controlled by the computer 150 or some other similar control means. Referring again to FIG. 5A, the light emitting diodes 520 of the light source array 510 can be adapted to be activated and de-activated in a controlled and coordinated manner so that the light emitted from the light emitting diodes 520 forms illuminated textual characters 530 and/or images 540 upon the surface of the scanning tube 140 as viewed by a patient within the scanning tube 140. This may be accomplished, for example, using information regarding the then current location of the light source array 510 relative to the scanning tube 140, the rate of speed at which the light source array 510 is rotating around the scanning tube, and other parameters regarding the light source array 510, the light emitting diodes 520 of the light source array 510. Many modern CT systems have high resolution position resolvers which can be used for this purpose. Depending upon the color of the light emitting diodes 520 of the light source array 510, the textual characters 530 or images 540 may be projected upon the scanning tube 140 in a variety of different colors.

The ability to project textual characters 530 and/or images 540 upon the scanning tube 140 may be employed to convey information to a patient within the scanning tube 140. For example, certain textual characters 530 and/or images 540 could be used as an indicator to instruct the patient to hold his or her breath or perform some other action. Also, certain textual characters 530 and/or images 540 could be used to indicate different stages of the imaging procedure. For example, textual characters, such as letters, numbers or other symbols, could be projected on the scanning tube in a countdown fashion to indicate the amount of time that is left in a particular scanning procedure or how long the patient should hold his or her breath. In addition, as previously discussed, the altering of the brightness, color, or some other characteristic of the light emitted from the light emitting diodes 520 of the light source array 510 could also be used to convey information to a patient within the scanning tube 140.

Figure 6:
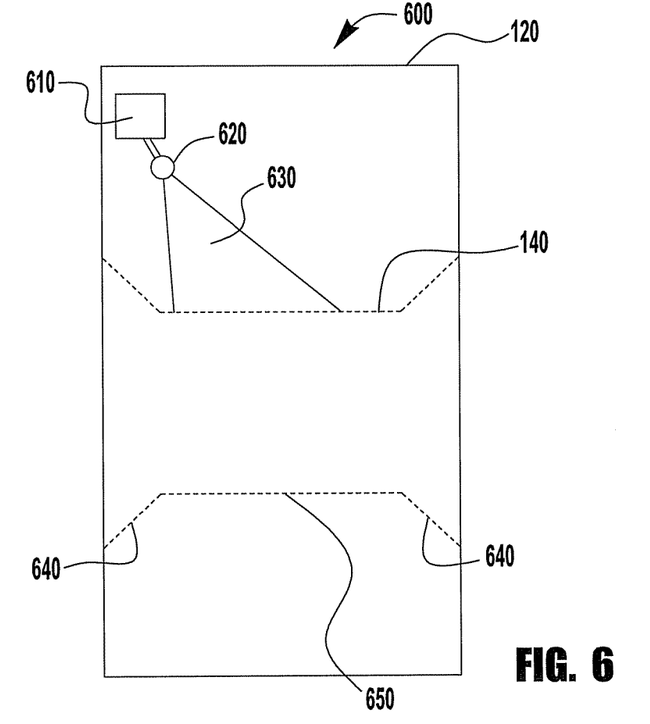
FIG. 6 is a right side elevational cut-away view of a fifth embodiment of the scanning tube illumination apparatus with the scanning tube depicted in broken lines.

Referring now to FIG. 6, a fifth embodiment of the scanning tube illumination apparatus 600 is shown. The illumination apparatus 600 includes at least one projector 610 mounted on the rotating gantry. The projector may include an optional lens 620 or a plurality of lenses to orient and project the image. The projector 610 is adapted to project an illuminated projection 630 upon the surface of the scanning tube 140. The projector 610 may serve simply to illuminate the scanning tube 140 or it may be used to project textual characters and/or images onto the scanning tube 140. The projector 610 may be located at various locations within the stationary gantry 120 or some other portion of the CT imaging system 100. The projector 610 may rotate with respect to the scanning tube 140 or it may remain stationary. The projector 610 may be used alone or it may be used in conjunction with any of the other embodiments of the illumination apparatus described herein. The scanning tube 140 of the embodiment of the illumination apparatus 600 illustrated in FIG. 6 includes frustoconical end sections 640 at each end of the scanning tube where the internal diameter of the scanning tube is greater than at its central portion 650. It should be understood that the illustrated embodiment of illumination apparatus 600, as well as any of the other embodiments of the illumination apparatus disclosed herein, can be adapted for use with scanning tubes 140 of various sizes, shapes and configurations.

Figure 7:
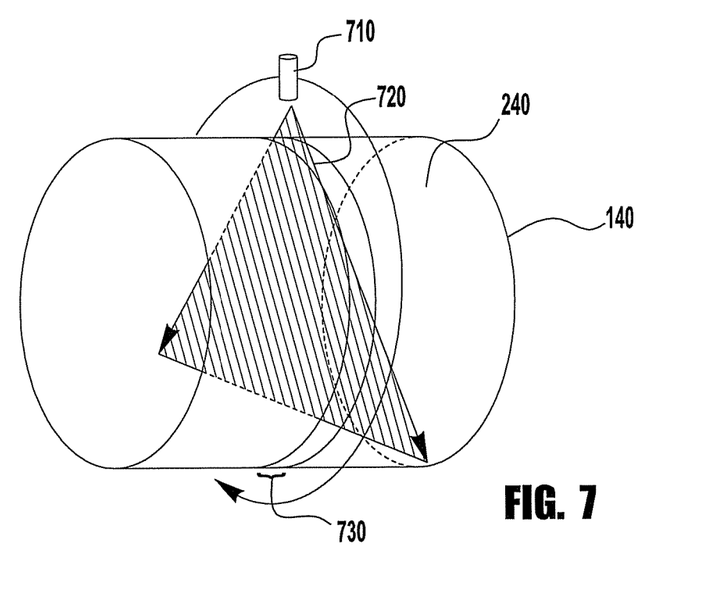
FIG. 7 is a perspective view of a scanning tube and a laser patient location device.

Referring now to FIG. 7, a conventional laser locator 710 is shown in use with a scanning tube 140. Laser locators 710 can optionally be used with various CT imaging systems to facilitate the proper location and orientation of a patient within the scanning tube. Laser locator 710 emits a laser light beam 720 through the scanning tube 140 to indicate the appropriate location for the placement of a patient within the scanning tube 140. When such a laser locator 710 is used in conjunction with an etched, frosted or otherwise translucent scanning tube 140 according to one of the embodiments of the illumination apparatus disclosed herein, an un-etched (i.e., transparent or nearly transparent) portion 730 of the scanning tube 140 may be optionally provided through which the laser light beam 720 emitted by the laser locator 710 may pass unobstructed. This optional un-etched portion 730 of the scanning tube can be used in connection with any of the embodiments of the illumination apparatus disclosed herein. Such embodiments can be useful in interventional procedures or in treatment planning scans to help locate, identify, or fix positions on or about the patient.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof. The invention may take form in various components and arrangements, combinations and sub-combinations of the elements of the disclosed embodiments. The drawings are only for purposes of illustrating the preferred embodiments and are not to be construed as limiting the invention.

Having thus described the preferred embodiments, the invention is now claimed to be:

1. A scanning tube illumination apparatus for use in a medical imaging apparatus and comprising:
    a scanning tube having a side wall; and
    at least one light source which emits light that travels through the side wall of the scanning tube thereby illuminating the side wall;
    wherein the scanning tube has an outer surface and wherein the at least one light source is adapted to rotate around the scanning tube to emit light that enters the side wall of the scanning tube through the outer surface and travels through the side wall thereby illuminating the side wall.

2. The illumination apparatus of claim 1, wherein the at least one light source comprises a light emitting diode.

3. The illumination apparatus of claim 1, wherein at least a portion of the side wall is translucent.

4. The illumination apparatus of claim 3, wherein at least a portion of the side wall is etched.

5. The illumination apparatus of claim 1, wherein the at least one light source is adapted to rotate in concert with at least one x-ray source or at least one x-ray detector unit that is also adapted to rotate around the scanning tube.

6. The illumination apparatus of claim 1, wherein the at least one light source comprises a light source array.

7. The illumination apparatus of claim 6, wherein the at least one light source array comprises a plurality of light emitting diodes.

8. The illumination apparatus of claim 6, wherein the light source array is adapted to selectively project textual characters, images, or both textual characters and images upon the side wall of the scanning tube.

9. The illumination apparatus of claim 1, wherein at least a first portion of the side wall is translucent and at least a second portion of the side wall is transparent to permit unobstructed passage of a laser light beam emitted by a laser locator through the side wall.

10. The illumination apparatus of claim 1, wherein the illumination apparatus is adapted for use in a medical imaging apparatus during an interventional procedure.

11. The illumination apparatus of claim 1, wherein the illumination apparatus comprises at least one projector.

12. A medical imaging apparatus comprising:
    an illumination apparatus, the illumination apparatus comprising:
    a scanning tube with a side wall; and
    at least one light source which emits light that travels through the side wall of the scanning tube thereby illuminating the side wall;
    wherein the scanning tube has an outer surface and wherein the at least one light source is adapted to rotate around the scanning tube to emit light that enters the side wall of the scanning tube through the outer surface and travels through the side wall thereby illuminating the side wall.

13. The medical imaging apparatus of claim 12, wherein at least a portion of the side wall is etched.

14. The medical imaging apparatus of claim 12, wherein the at least one light source comprises a light source array.

15. The medical imaging apparatus of claim 14, wherein the at least one light source array comprises a plurality of light emitting diodes.

16. The medical imaging apparatus of claim 14, wherein the light source array is adapted to selectively project textual characters, images, or both textual characters and images upon the side wall of the scanning tube.

17. A method of imaging comprising the steps of:
collecting imaging data from an imaged subject in an examination region of a scanning tube having a side wall and an outer surface;
providing an illumination apparatus comprising at least one light source which is adapted to rotate around the scanning tube to emit light that enters the side wall of the scanning tube through the outer surface and travels through the side wall thereby illuminating the side wall; and
using the illumination apparatus to illuminate at least a portion of the examination region during at least a portion of the step of collecting imaging data.

18. The method of imaging of claim 17, wherein the step of illuminating further comprises conveying a message to the imaged subject located in the examination region.

19. The method of imaging of claim 17, wherein the step of illuminating is non-continuous.

* * * * *